(12) United States Patent
Vaartstra et al.

(10) Patent No.: US 7,858,815 B2
(45) Date of Patent: Dec. 28, 2010

(54) SYSTEMS AND METHODS FOR FORMING TANTALUM OXIDE LAYERS AND TANTALUM PRECURSOR COMPOUNDS

(75) Inventors: Brian A. Vaartstra, Nampa, ID (US); Timothy A. Quick, Boise, ID (US)

(73) Assignee: Micron Technology, Inc., Boise, ID (US)

(*) Notice: Subject to any disclaimer, the term of this patent is extended or adjusted under 35 U.S.C. 154(b) by 193 days.

(21) Appl. No.: 12/106,510

(22) Filed: Apr. 21, 2008

(65) Prior Publication Data

US 2008/0227303 A1 Sep. 18, 2008

Related U.S. Application Data

(62) Division of application No. 10/924,096, filed on Aug. 23, 2004, now Pat. No. 7,368,402, which is a division of application No. 10/230,243, filed on Aug. 28, 2002, now Pat. No. 7,030,042.

(51) Int. Cl.
*C07F 9/00* (2006.01)
*H01L 21/31* (2006.01)

(52) U.S. Cl. .................................. 556/42; 438/785
(58) Field of Classification Search .................. 556/42
See application file for complete search history.

(56) References Cited

U.S. PATENT DOCUMENTS

| | | | |
|---|---|---|---|
| 4,525,468 A | 6/1985 | Mack et al. | |
| 5,256,244 A | 10/1993 | Ackerman | |
| 5,401,305 A | 3/1995 | Russo et al. | |
| 5,462,014 A | 10/1995 | Awaya et al. | |
| 5,468,687 A | 11/1995 | Carl et al. | |
| 5,480,488 A | 1/1996 | Bittner et al. | |
| 5,487,918 A | 1/1996 | Akhtar | |
| 5,599,387 A | 2/1997 | Neuman et al. | |
| 5,780,115 A | 7/1998 | Park et al. | |
| 5,820,664 A | 10/1998 | Gardiner et al. | |
| 5,820,994 A | 10/1998 | Gotoh et al. | |
| 5,863,337 A | 1/1999 | Neuman et al. | |
| 5,948,322 A | 9/1999 | Baum et al. | |
| 5,989,623 A | 11/1999 | Chen et al. | |
| 6,037,001 A | 3/2000 | Kaloyeros et al. | |
| 6,118,146 A | 9/2000 | Park et al. | |
| 6,133,086 A | 10/2000 | Huang et al. | |
| 6,146,959 A | 11/2000 | DeBoer et al. | |
| 6,200,658 B1 | 3/2001 | Walther et al. | |
| 6,200,847 B1 | 3/2001 | Kishiro | |
| 6,207,302 B1 | 3/2001 | Sugiura et al. | |
| 6,265,260 B1 | 7/2001 | Alers et al. | |
| 6,328,947 B1 | 12/2001 | Monden et al. | |
| 6,448,187 B2 | 9/2002 | Yau et al. | |
| 6,461,982 B2 | 10/2002 | DeBoer et al. | |
| 6,482,477 B1 | 11/2002 | Westhoff et al. | |
| 6,487,918 B1 | 12/2002 | DeAngelis | |
| 6,534,395 B2 | 3/2003 | Werkhoven et al. | |
| 6,548,424 B2 | 4/2003 | Putkonen | |
| 6,596,602 B2 | 7/2003 | Iizuka et al. | |
| 6,784,049 B2 | 8/2004 | Vaartstra | |
| 6,919,243 B2 | 7/2005 | Chung et al. | |
| 6,932,867 B2 | 8/2005 | Ritala et al. | |
| 6,939,579 B2 | 9/2005 | Bondestam et al. | |
| 6,998,014 B2 | 2/2006 | Chen et al. | |
| 7,030,042 B2 | 4/2006 | Vaartstra et al. | |
| 7,368,402 B2 | 5/2008 | Vaartstra et al. | |
| 2001/0036752 A1 | 11/2001 | DeBoer et al. | |
| 2001/0041250 A1 | 11/2001 | Werkhoven et al. | |
| 2002/0094634 A1 | 7/2002 | Chung et al. | |
| 2002/0102810 A1 | 8/2002 | Iizuka et al. | |
| 2002/0157611 A1 | 10/2002 | Bondestam et al. | |
| 2003/0143328 A1 | 7/2003 | Chen et al. | |
| 2003/0188682 A1 | 10/2003 | Tois et al. | |
| 2004/0018735 A1 | 1/2004 | Park et al. | |
| 2004/0043633 A1 | 3/2004 | Vaartstra | |
| 2005/0009266 A1 | 1/2005 | Vaartstra | |
| 2006/0178019 A1 | 8/2006 | Senzaki et al. | |

FOREIGN PATENT DOCUMENTS

| | | |
|---|---|---|
| EP | 1205574 | 5/2002 |
| JP | 2001-181288 A | * 12/1999 |
| WO | WO 95/26355 | 10/1995 |
| WO | WO 01/40541 | 6/2001 |

OTHER PUBLICATIONS

Chaneliere et al., "Dielectric Permittivity of Amorphous and Hexagonal Electron Cyclotron Resonance Plasma Deposited $Ta_2O_5$ Thin Films," *Electrochemical and Solid-State Letters*, Jun. 1999; 2(6):291-3.

Grant & Hackh's Chemical Dictionary, McGraw-Hill Book Company, $5^{th}$ edition, 1987:221.

Hawley, *The Condensed Chemical Dictionary*, $10^{th}$ Edition, Van Nostrand Reinhold Co., New York, 1981; 225-226.

Jiménez et al., "Deposition of $Ta_2O_5$ and $(Tio_2)$-$(Ta_2O_5)$ films from $Ta(OEt)_4(DMAE)$ and $Ti(OEt)_2(DMAE)_2$, by IMOCVD," *J. Phys. IV France*, 1999; 9:Pr8-569-Pr8-573.

Kishiro et al., "Structure and Electrical Properties of Thin $Ta_2O_5$ Deposited on Metal Electrodes," *Jpn. J. Appl. Phys.*, Mar. 1998; 37(3B):1336-9.

(Continued)

*Primary Examiner*—Porfirio Nazario Gonzalez
(74) *Attorney, Agent, or Firm*—Wells St. John P.S.

(57) ABSTRACT

A method of forming (and apparatus for forming) a tantalum oxide layer on a substrate, particularly a semiconductor substrate or substrate assembly, using a vapor deposition process and a tantalum precursor compound that includes alkoxide ligands, for example.

24 Claims, 3 Drawing Sheets

OTHER PUBLICATIONS

Lin et al., "$Ta_2O_5$ thin films with exceptionally high dielectric constant," *Applied Physics Letter*, Apr. 1999; 74(16):2370-2.

"Material Safety Data Sheet- Catalog # 235733, Name: 1,1,3,3-Tetramethyldisiloxane, 97%" *Aldrich Chemical Co., Inc.* [online]. [retrieved Jun. 23, 2003]. Retrieved from the internet<http://infonew.sigma-aldrich.com/cgi-bin/gx.cgi/Applogic+MSDSInfo.ReturnMSDS>;3 pgs. Valid May-Jul. 2003.

"Material Safety Data Sheet- Catalog # 326739, Name: Hexamethyldisiloxane, 99.5+%, NMR Grade," *Aldrich Chemical Co., Inc.* [online]. [retrieved Jun. 23, 2003]. Retrieved from the internet: <http://infonew.sigma-aldrich.com/cgi-bin/gx.cgi/Applogic+MSDSInfo.ReturnMSDS>;3 pgs. Valid May-Jul. 2003.

"Refractory" and "Refractory metal," *Webster's New Universal Unabridged Dictionary*, Avenel, New Jersey, 1992; p. 1207.

Vehkamäki et al., "Growth of $SrTiO_3$ and $BaTiO_3$ Thin Films by Atomic Layer Deposition," *Electrochemical and Solid-State Letters*, Oct. 1999; 2(10):504-506.

\* cited by examiner

SYSTEMS AND METHODS FOR FORMING TANTALUM OXIDE LAYERS AND TANTALUM PRECURSOR COMPOUNDS

This is a divisional of application Ser. No. 10/924,096, filed Aug. 23, 2004, (pending), which is a divisional of application Ser. No. 10/230,243, filed Aug. 28, 2002, (issued as U.S. Pat. No. 7,030,042), which are all incorporated herein by reference.

FIELD OF THE INVENTION

This invention relates to methods of forming a tantalum oxide layer on a substrate using a tantalum precursor compound containing organo-oxide (e.g., alkoxide) ligands during a vapor deposition process, and to tantalum percursor compounds. The precursor compounds and methods are particularly suitable for the formation of a tantalum oxide layer on semiconductor substrates or substrate assemblies.

BACKGROUND OF THE INVENTION

High quality thin oxide films of metals, such as $Ta_2O_5$ layers, deposited on semiconductor wafers have recently gained interest for use in memories (e.g., dynamic random access memory (DRAM) devices, static random access memory (SRAM) devices, and ferroelectric memory (FE-RAM) devices). These materials, particularly $Ta_2O_5$, have very high dielectric constants and therefore are attractive as capacitor dielectrics and gate dielectrics.

Suitable metal oxides are typically delivered to a substrate in the vapor phase. Vapor deposition processes, which includes chemical vapor deposition (CVD) and atomic layer deposition (ALD), are very appealing as they provide for excellent control of dielectric uniformity and thickness on a substrate.

Many oxides are difficult to deliver using vapor deposition technology. Many precursors are sensitive to thermal decomposition. Also, many precursors have vapor pressures that are too low for effective vapor deposition. For example, molecules containing certain low-valent metals tend to aggregate, which causes poor volatility. Many other precursors that have sufficient volatility, such as tantalum pentaethoxide, require rather high temperatures to attain significant vapor pressure. This can present certain technical difficulties with delivery of the vapor to the deposition chamber. The modified precursor, tantalum tetraethoxydimethylaminoethoxide, has significantly higher vapor pressure; however, the presence of nitrogen may be a problem with migration into transistors.

Thus, there is a continuing need for methods and materials for the deposition of tantalum oxide films using vapor deposition processes on substrates, particularly semiconductor structures such as random access memory devices.

SUMMARY OF THE INVENTION

This invention provides methods of vapor depositing a tantalum oxide layer on a substrate, particularly a semiconductor substrate or substrate assembly. These vapor deposition methods involve forming the layer by combining a tantalum precursor compound (i.e., one or more tantalum precursor compounds), preferably containing alkoxide ligands, with one or more reaction gases and/or one or more other metal-containing precursor compounds. The tantalum oxide layer can be used as a dielectric layer, for example, in a semiconductor structure.

In one embodiment, the present invention provides a method of forming a tantalum oxide layer on a substrate, preferably in a process for manufacturing a semiconductor structure. The method includes: providing a substrate (preferably a semiconductor substrate or substrate assembly); providing a vapor that includes one or more precursor compounds of the formula $Ta(OR^1)_x(O-R^2-OR^3)_y$ (Formula I), wherein each R is an organic group, x=3-4, and y=1-2; optionally providing one or more sources of a reaction gas; and directing the one or more vaporized precursor compounds and the one or more optional reaction gases to the substrate to form a tantalum oxide layer on one or more surfaces of the substrate. In addition to, or in place of, the reaction gas, the method can include providing a vapor that includes one or more metal-containing precursor compounds different than $Ta(OR^1)_x(O-R^2-OR^3)_y$, and directing this vapor to the substrate.

The present invention also provides a method of manufacturing a memory device. The method includes: providing a substrate (preferably a semiconductor substrate or substrate assembly such as a silicon wafer) having a first electrode thereon; providing a vapor including one or more precursor compounds of the formula $Ta(OR^1)_x(O-R^2-OR^3)_y$ (Formula I), wherein each R is an organic group, x=3-4, and y=1-2; optionally providing one or more sources of a reaction gas (e.g., an oxidizing gas); and directing the one or more vaporized precursor compounds and the one or more optional reaction gases to the substrate to form a tantalum oxide dielectric layer on the first electrode of the substrate; and forming a second electrode on the dielectric layer. In addition to, or in place of, the reaction gas, the method can include providing a vapor that includes one or more metal-containing precursor compounds different from $Ta(OR^1)_x(O-R^2-OR^3)_y$, and directing this vapor to the substrate.

In another embodiment, the present invention provides a compound of the formula $Ta(OR^1)_x(O-R^2-OR^3)_y$, wherein each $R^3$ group is an isopropyl group, $R^1$ and $R^2$ are each independently a (C1-C10) organic group, x=3-4, and y=1-2. Preferably, $R^1$ and $R^2$ are each independently a (C1-C5) organic group, more preferably a (C1-C3) organic group, and even more preferably a (C1-C2) organic moiety. Particular examples include $Ta(OEt)_4(OCH_2CH_2O^iPr)$ or $Ta(OMe)_4(OCH_2CH_2O^iPr)$ wherein Me methyl, Et ethyl, and $^iPr$=isopropyl.

The present invention also provides a vapor deposition apparatus that includes: a vapor deposition chamber having a substrate (preferably a semiconductor substrate or substrate assembly such as a silicon wafer) positioned therein; and one or more vessels that include one or more precursor compounds of the formula $Ta(OR^1)_x(O-R^2-OR^3)_y$, wherein each $R^3$ group is an isopropyl group, $R^1$ and $R^2$ are each independently a (C1-C10) organic group, x=3-4, and y=1-2. The apparatus can further include one or more sources of an inert carrier gas for transferring the precursors to the vapor deposition chamber, one or more sources of a reaction gas, and one or more vessels that include one or more metal-containing precursor compounds different from $Ta(OR^1)_x(O-R^2-OR^3)_y$.

The methods of the present invention can utilize a chemical vapor deposition (CVD) process, which can be pulsed, or an atomic layer deposition (ALD) process (a self-limiting vapor deposition process that includes a plurality of deposition cycles, typically with purging between the cycles). Preferably, the methods of the present invention use ALD. For certain ALD processes, the tantalum oxide layer is formed by alternately introducing one or more precursor compounds of Formula I and reaction gases into the deposition chamber during each deposition cycle."

"Semiconductor substrate" or "substrate assembly" as used herein refers to a semiconductor substrate such as a base semiconductor layer or a semiconductor substrate having one or more layers, structures, or regions formed thereon. A base semiconductor layer is typically the lowest layer of silicon material on a wafer or a silicon layer deposited on another material, such as silicon on sapphire. When reference is made to a substrate assembly, various process steps may have been previously used to form or define regions, junctions, various structures or features, and openings such as capacitor plates or barriers for capacitors.

"Precursor compound" as used herein refers to a compound capable of forming, either alone or with other precursor compounds, a tantalum oxide layer on a substrate in a vapor deposition process. Preferably, the precursor compounds form volatile by-products, and include tantalum. Precursor compounds containing metals other than tantalum can also be used to make more complex layers containing tantalum oxide.

"Layer" as used herein refers to any metal-containing layer that can be formed on a substrate from the precursor compounds of this invention using a vapor deposition process. The term "layer" is meant to include layers specific to the semiconductor industry, such as "barrier layer," "dielectric layer," and "conductive layer." (The term "layer" is synonymous with the term "film" frequently used in the semiconductor industry.) The term "layer" is also meant to include layers found in technology outside of semiconductor technology, such as coatings on glass.

"Deposition process" and "vapor deposition process" as used herein refer to a process in which a metal-containing layer is formed on one or more surfaces of a substrate (e.g., a doped polysilicon wafer) from vaporized precursor compound(s). Specifically, one or more metal precursor compounds are vaporized and directed to one or more surfaces of a heated substrate (e.g., semiconductor substrate or substrate assembly) placed in a deposition chamber. These precursor compounds form (e.g., by reacting or decomposing) a non-volatile, thin, uniform, metal-containing layer on the surface(s) of the substrate. For the purposes of this invention, the term "vapor deposition process" is meant to include both chemical vapor deposition processes (including pulsed chemical vapor deposition processes) and atomic layer deposition processes.

"Chemical vapor deposition" (CVD) as used herein refers to a vapor deposition process wherein the desired layer is deposited on the substrate from vaporized metal precursor compounds and any reaction gases used within a deposition chamber with no effort made to separate the reaction components. In contrast to a "simple" CVD process that involves the substantial simultaneous use of the precursor compounds and any reaction gases, "pulsed" CVD alternately pulses these materials into the deposition chamber, but does not rigorously avoid intermixing of the precursor and reaction gas streams, as is typically done in atomic layer deposition or ALD (discussed in greater detail below).

"Atomic layer deposition" (ALD) as used herein refers to a vapor deposition process in which numerous consecutive deposition cycles are conducted in a deposition chamber. Typically, during each cycle the metal precursor is chemisorbed to the substrate surface; excess precursor is purged out; a subsequent precursor and/or reaction gas is introduced to react with the chemisorbed layer; and excess reaction gas (if used) and by-products are removed. As compared to the one cycle chemical vapor deposition (CVD) process, the longer duration multi-cycle ALD process allows for improved control of layer thickness by self-limiting layer growth and minimizing detrimental gas phase reactions by separation of the reaction components. The term "atomic layer deposition" as used herein is also meant to include the related terms "atomic layer epitaxy" (ALE) (see U.S. Pat. No. 5,256,244 (Ackerman)), molecular beam epitaxy (MBE), gas source MBE, organometallic MBE, and chemical beam epitaxy when performed with alternating pulses of precursor compound(s), reaction gas and purge (i.e., inert carrier) gas.

"Chemisorption" as used herein refers to the chemical adsorption of vaporized reactive precursor compounds on the surface of a substrate. The adsorbed species are irreversibly bound to the substrate surface as a result of relatively strong binding forces characterized by high adsorption energies (>30 kcal/mol), comparable in strength to ordinary chemical bonds. The chemisorbed species are limited to the formation of a monolayer on the substrate surface. (See "The Condensed Chemical Dictionary", 10th edition, revised by G. G. Hawley, published by Van Nostrand Reinhold Co., New York, 225 (1981)). The technique of ALD is based on the principle of the formation of a saturated monolayer of reactive precursor molecules by chemisorption. In ALD one or more appropriate reactive precursor compounds are alternately introduced (e.g., pulsed) into a deposition chamber and chemisorbed onto the surfaces of a substrate. Each sequential introduction of a reactive precursor compound is typically separated by an inert carrier gas purge. Each precursor compound co-reaction adds a new atomic layer to previously deposited layers to form a cumulative solid layer. The cycle is repeated, typically for several hundred times, to gradually form the desired layer thickness. It should be understood, however, that ALD can use one precursor compound and one reaction gas.

DETAILED DESCRIPTION OF PREFERRED EMBODIMENTS OF THE INVENTION

Figure 1:
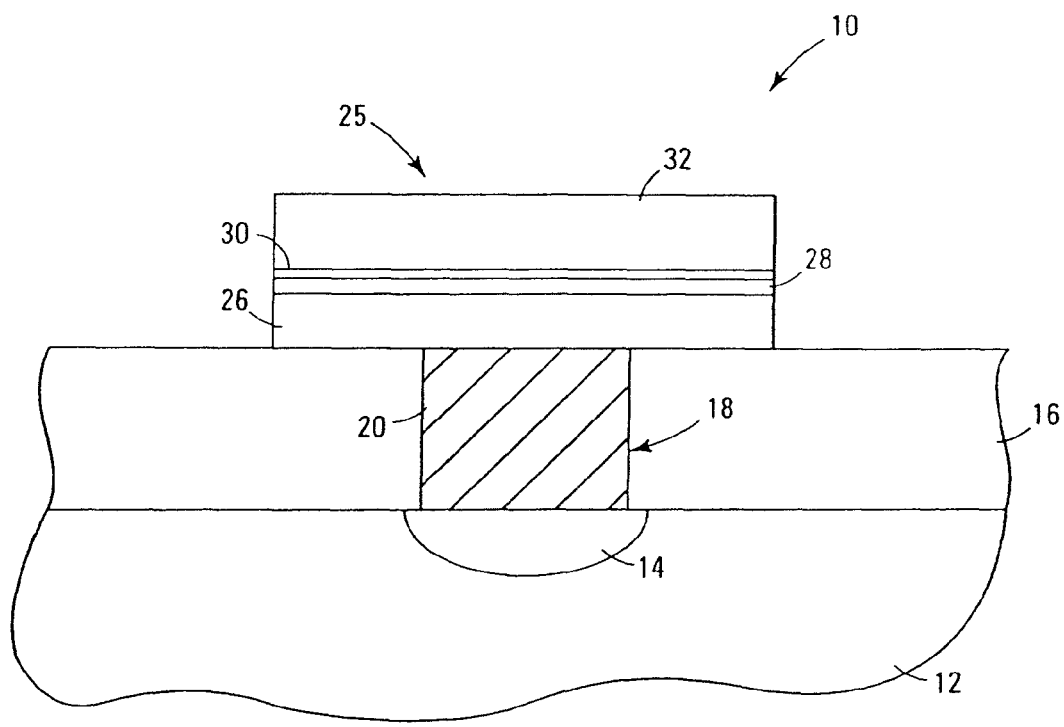
FIGS. 1-3 are exemplary capacitor constructions.

The present invention provides methods of forming a tantalum oxide layer on a substrate (preferably a semiconductor substrate or substrate assembly) using one or more precursor compounds of the formula $Ta(OR^1)_x(O-R^2-OR^3)_y$, (Formula I) wherein each R is an organic group, x=3-4, and y=1-2. Preferably, each R is independently of a size that allows for sufficient volatility at moderate vaporizing temperatures.

The layers or films formed can be in the form of tantalum oxide-containing films, wherein the tantalum-oxide is doped with other metals, such as strontium. Thus, the term "tantalum oxide" films or layers encompass just tantalum oxide as well as tantalum oxide-containing films or layers. Thus, precursor compounds other than those described above, particularly precursor compounds containing metals other than tantalum, can be used in the methods of the present invention. Such compounds can be readily selected by one of skill in the art.

The substrate on which the metal-containing layer is formed is preferably a semiconductor substrate or substrate assembly. Any suitable semiconductor material is contemplated, such as for example, conductively doped polysilicon (for this invention simply referred to as "silicon"). A substrate assembly may also contain a layer that includes platinum, iridium, rhodium, ruthenium, ruthenium oxide, titanium nitride, tantalum nitride, tantalum-silicon-nitride, silicon dioxide, aluminum, gallium arsenide, glass, etc., and other existing or to-be-developed materials used in semiconductor constructions, such as dynamic random access memory (DRAM) devices, and static random access memory (SRAM) devices, and ferroelectric memory (FERAM) devices, for example.

Substrates other than semiconductor substrates or substrate assemblies can be used in methods of the present invention. These include, for example, fibers, wires, etc. If the substrate is a semiconductor substrate or substrate assembly, the layers can be formed directly on the lowest semiconductor surface of the substrate, or they can be formed on any of a variety of the layers (i.e., surfaces) as in a patterned wafer, for example.

The precursor compounds (i.e., precursor complexes) of the formula $Ta(OR^1)_x(O-R^2-OR^3)_y$ (Formula I) wherein each R is an organic group, x=3-4, and y=1-2 are neutral complexes. Preferably, each R is independently of a size that allows for sufficient volatility at moderate vaporizing temperatures. Typically, this means that each organic group includes up to 10 carbon atoms optionally substituted with or replaced by silicon and/or fluorine atoms. That is, typically if silicon is present it replaces one of the 10 carbon atoms. If fluorine is present it replaces one or more hydrogen atoms attached to carbon.

As used herein, the term "organic group" means a hydrocarbon group (with optional elements other than carbon and hydrogen, such as oxygen, nitrogen, sulfur, and silicon) that is classified as an aliphatic group, cyclic group, or combination of aliphatic and cyclic groups (e.g., alkaryl and aralkyl groups). In the context of the present invention, the organic groups are those that do not interfere with the formation of a tantalum oxide film. Preferably, they are of a type and size that do not interfere with the formation of a tantalum oxide film using chemical vapor deposition techniques. The term "aliphatic group" means a saturated or unsaturated linear or branched hydrocarbon group. This term is used to encompass alkyl, alkenyl, and alkynyl groups, for example. The term "alkyl group" means a saturated linear or branched hydrocarbon group including, for example, methyl, ethyl, isopropyl, t-butyl, and the like. The term "alkenyl group" means an unsaturated, linear or branched hydrocarbon group with one or more carbon-carbon double bonds, such as a vinyl group. The term "alkynyl group" means an unsaturated, linear or branched hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polynuclear aromatic hydrocarbon group. The term "heterocyclic group" means a closed ring hydrocarbon in which one or more of the atoms in the ring is an element other than carbon (e.g., nitrogen, oxygen, sulfur, etc.).

As a means of simplifying the discussion and recitation of certain terminology used throughout this application, the terms "group" and "moiety" are used to differentiate between chemical species that allow for substitution or that may be substituted and those that do not allow or may not be so substituted. Thus, when the term "group" is used to describe a chemical substituent, the described chemical material includes the unsubstituted group and that group with Si or F atoms. Where the term "moiety" is used to describe a chemical compound or substituent, only an unsubstituted chemical material is intended to be included. For example, the phrase "alkyl moiety" is limited to the inclusion of only pure open chain saturated hydrocarbon alkyl substituents, such as methyl, ethyl, propyl, t-butyl, and the like.

Preferably, $R^1$ is a (C1-C5) organic group, more preferably a (C1-C3) organic group, and most preferably a (C1-C2) organic moiety. Preferably, $R^2$ is a (C1-C5) organic group, more preferably a (C1-C3) organic group, and most preferably a (C2) organic moiety. Preferably, $R^3$ is a (C1-C5) organic group, more preferably a (C2-C5) organic group, and most preferably a (C3-C5) organic moiety.

Particularly preferred complexes of Formula I include $Ta(OEt)_4(OCH_2CH_2O^iPr)$ and $Ta(OMe)_4(OCH_2CH_2O^iPr)$ where in Me methyl, Et=ethyl, and $^iPr$=isopropyl.

The complexes of the present invention can be prepared by a variety of methods known to one of skill in the art. For example, complexes of Formula I can be prepared by combining $Ta(OR^1)_5$ with $HO-R^2-OR^3$ with heating.

Various precursor compounds can be used in various combinations, optionally with one or more organic solvents, to form a precursor composition. The precursor compounds may be liquids or solids at room temperature (preferably, they are liquids at the vaporization temperature). Typically, they are liquids sufficiently volatile to be employed using known vapor deposition techniques. However, as solids they may also be sufficiently volatile that they can be vaporized or sublimed from the solid state using known vapor deposition techniques. If they are less volatile solids, they are preferably sufficiently soluble in an organic solvent or have melting points below their decomposition temperatures such that they can be used in flash vaporization, bubbling, microdroplet formation techniques, etc. Herein, vaporized precursor compounds may be used either alone or optionally with vaporized molecules of other precursor compounds or optionally with vaporized solvent molecules, if used. As used herein, "liquid" refers to a solution or a neat liquid (a liquid at room temperature or a solid at room temperature that melts at an elevated temperature). As used herein, "solution" does not require complete solubility of the solid but may allow for some undissolved solid, as long as there is a sufficient amount of the solid delivered by the organic solvent into the vapor phase for chemical vapor deposition processing. If solvent dilution is used in deposition, the total molar concentration of solvent vapor generated may also be considered as a inert carrier gas.

The solvents that are suitable for this application can be one or more of the following: aliphatic hydrocarbons or unsaturated hydrocarbons (C3-C20, and preferably C5-C10, cyclic, branched, or linear), aromatic hydrocarbons (C5-C20, and preferably C5-C10), halogenated hydrocarbons, silylated hydrocarbons such as alkylsilanes, alkylsilicates, ethers, polyethers, thioethers, esters, lactones, ammonia, amides, amines (aliphatic or aromatic, primary, secondary, or tertiary), polyamines, nitrites, cyanates, isocyanates, thiocyanates, silicone oils, alcohols, or compounds containing combinations of any of the above or mixtures of one or more of the above. The compounds are also generally compatible with each other, so that mixtures of variable quantities of the precursor compounds will not interact to significantly change their physical properties.

The precursor compounds can be vaporized in the presence of an inert carrier gas if desired. Additionally, an inert carrier gas can be used in purging steps in an ALD process. The inert carrier gas is typically selected from the group consisting of nitrogen, helium, argon, and mixtures thereof. In the context of the present invention, an inert carrier gas is one that is generally unreactive with the complexes described herein and does not interfere with the formation of a tantalum oxide film (i.e., layer).

In the process of the present invention, the tantalum precursor compounds can be contacted with a reaction gas and/or other precursor compound at elevated temperatures to form a metal-containing film. A reaction gas is preferred. The reaction gas is preferably an oxidizing gas such as oxygen, water vapor, ozone, alcohol vapor, nitrogen oxides, sulfur oxides, hydrogen peroxide, and the like. Various combinations of carrier gases and/or reaction gases and/or other precursor compounds can be used in the methods of the present invention to form tantalum oxide films.

Methods of the present invention can be used to deposit a tantalum oxide film on a variety of substrates, such as a semiconductor wafer (e.g., silicon wafer, gallium arsenide wafer, etc.), glass plate, etc., and on a variety of surfaces of the substrates, whether it be directly on the substrate itself or on a layer of material deposited on the substrate as in a semiconductor substrate assembly. The film is deposited upon reacting or by thermal decomposition of complexes of Formula I. Preferably, the tantalum precursor compounds are liquid and used neat. Methods of the present invention preferably utilize vapor deposition techniques, such as flash vaporization, bubbling, etc.

The deposition process for this invention is a vapor deposition process. Vapor deposition processes are generally favored in the semiconductor industry due to the process capability to quickly provide highly conformal layers even within deep contacts and other openings. Chemical vapor deposition (CVD) and atomic layer deposition (ALD) are two vapor deposition processes often employed to form thin, continuous, uniform, metal-containing (preferably dielectric) layers onto semiconductor substrates. Using either vapor deposition process, typically one or more precursor compounds are vaporized in a deposition chamber and optionally combined with a reaction gas to form a metal-containing layer onto a substrate. It will be readily apparent to one skilled in the art that the vapor deposition process may be enhanced by employing various related techniques such as plasma assistance, photo assistance, laser assistance, as well as other techniques.

The final layer (preferably, a dielectric layer) formed preferably has a thickness in the range of about 10 Å to about 500 Å. More preferably, the thickness of the metal-containing layer is in the range of about 50 Å to about 150 Å.

Chemical vapor deposition (CVD) has been extensively used for the preparation of metal-containing layers, such as dielectric layers, in semiconductor processing because of its ability to provide highly conformal and high quality dielectric layers at relatively fast processing times. The desired precursor compounds are vaporized and then introduced into a deposition chamber containing a heated substrate with optional reaction gases and/or inert carrier gases. In a typical CVD process, vaporized precursors are contacted with one or more reaction gases at the substrate surface to form a layer (e.g., dielectric layer). The single deposition cycle is allowed to continue until the desired thickness of the layer is achieved.

Typical CVD processes generally employ precursor compounds in vaporization chambers that are separated from the process chamber wherein the deposition surface or wafer is located. For example, liquid precursor compounds are typically placed in bubblers and heated to a temperature at which they vaporize, and the vaporized liquid precursor compound is then transported by an inert carrier gas passing over the bubbler or through the liquid precursor compound. The vapors are then swept through a gas line to the deposition chamber for depositing a layer on substrate surface(s) therein. Many techniques have been developed to precisely control this process. For example, the amount of precursor material transported to the deposition chamber can be precisely controlled by the temperature of the reservoir containing the precursor compound and by the flow of an inert carrier gas bubbled through or passed over the reservoir.

Preferred embodiments of the precursor compounds described herein are particularly suitable for chemical vapor deposition (CVD). The deposition temperature at the substrate surface is preferably held at a temperature in a range of about 100° C. to about 600° C., more preferably in the range of about 200° C. to about 500° C. The deposition chamber pressure is preferably maintained at a deposition pressure of about 0.1 torr to about 10 torr. The partial pressure of precursor compounds in the inert carrier gas is preferably about 0.001 torr to about 10 torr.

Several modifications of the CVD process and chambers are possible, for example, using atmospheric pressure chemical vapor deposition, low pressure chemical vapor deposition (LPCVD), plasma enhanced chemical vapor deposition (PECVD), hot wall or cold wall reactors or any other chemical vapor deposition technique. Furthermore, pulsed CVD can be used, which is similar to ALD (discussed in greater detail below) but does not rigorously avoid intermixing of precursor and reactant gas streams. Also, for pulsed CVD, the deposition thickness is dependent on the exposure time, as opposed to ALD, which is self-limiting (discussed in greater detail below).

A typical CVD process may be carried out in a chemical vapor deposition reactor, such as a deposition chamber available under the trade designation of 7000 from Genus, Inc. (Sunnyvale, Calif.), a deposition chamber available under the trade designation of 5000 from Applied Materials, Inc. (Santa Clara, Calif.), or a deposition chamber available under the trade designation of Prism from Novelus, Inc. (San Jose, Calif.). However, any deposition chamber suitable for performing CVD may be used.

Alternatively, and preferably, the vapor deposition process employed in the methods of the present invention is a multi-cycle ALD process. Such a process is advantageous (particularly over a CVD process) in that in provides for optimum control of atomic-level thickness and uniformity to the deposited layer (e.g., dielectric layer) and to expose the metal precursor compounds to lower volatilization and reaction temperatures to minimize degradation. Typically, in an ALD process, each reactant (e.g., precursor compound and reaction gas) is pulsed sequentially onto a suitable substrate, typically at deposition temperatures of about 25° C. to about 400° C. (preferably about 150° C. to about 300° C.), which is generally lower than presently used in CVD processes. Under such conditions the film growth is typically self-limiting (i.e., when the reactive sites on a surface are used up in an ALD process, the deposition generally stops), insuring not only excellent conformality but also good large area uniformity plus simple and accurate thickness control. Due to alternate dosing of the precursor compound(s) and/or reaction gas(es), detrimental vapor-phase reactions are inherently eliminated, in contrast to the CVD process that is carried out by continuous correction of the precursors and/or reaction gases (See Vehkamäki et al, "Growth of $SrTiO_3$ and $BaTiO_3$ Thin Films by Atomic Layer Deposition," Electrochemical and Solid-State Letters, 2(10):504-506 (1999)).

A typical ALD process includes exposing an initial substrate to a first chemical species (e.g., tantalum precursor compound of Formula I) to accomplish chemisorption of the species onto the substrate. Theoretically, the chemisorption forms a monolayer that is uniformly one atom or molecule thick on the entire exposed initial substrate. In other words, a saturated monolayer. Practically, chemisorption might not occur on all portions of the substrate. Nevertheless, such an imperfect monolayer is still a monolayer in the context of the present invention. In many applications, merely a substantially saturated monolayer may be suitable. A substantially saturated monolayer is one that will still yield a deposited layer exhibiting the quality and/or properties desired for such layer.

The first species is purged from over the substrate and a second chemical species (e.g., reaction gas such as alcohol vapor) is provided to react with the first monolayer of the first species. The second species is then purged and the steps are repeated with exposure of the second species monolayer to the first species. In some cases, the two monolayers may be of the same species. As an option, the second species can react with the first species, but not chemisorb additional material thereto. That is, the second species can cleave some portion of the chemisorbed first species, altering such monolayer without forming another monolayer thereon. Also, a third species (e.g. different precursor compound containing tantalum or some other metal or different reaction gas) or more may be successively chemisorbed (or reacted) and purged just as described for the first and second species.

Purging may involve a variety of techniques including, but not limited to, contacting the substrate and/or monolayer with a carrier gas and/or lowering pressure to below the deposition pressure to reduce the concentration of a species contacting the substrate and/or chemisorbed species. Examples of carrier gases include $N_2$, Ar, He, etc. Purging may instead include contacting the substrate and/or monolayer with any substance that allows chemisorption by-products to desorb and reduces the concentration of a contacting species preparatory to introducing another species. The contacting species may be reduced to some suitable concentration or partial pressure known to those skilled in the art based on the specifications for the product of a particular deposition process.

ALD is often described as a self-limiting process, in that a finite number of sites exist on a substrate to which the first species may form chemical bonds. The second species might only bond to the first species and thus may also be self-limiting. Once all of the finite number of sites on a substrate are bonded with a first species, the first species will often not bond to other of the first species already bonded with the substrate. However, process conditions can be varied in ALD to promote such bonding and render ALD not self-limiting. Accordingly, ALD may also encompass a species forming other than one monolayer at a time by stacking of a species, forming a layer more than one atom or molecule thick.

The described method indicates the "substantial absence" of the second species (e.g., reaction gas) during chemisorption of the first species (e.g., tantalum precursor compound of Formula I) since insignificant amounts of the second species might be present. According to the knowledge and the preferences of those with ordinary skill in the art, a determination can be made as to the tolerable amount of second species and process conditions selected to achieve the substantial absence of the second species.

Thus, during the ALD process, numerous consecutive deposition cycles are conducted in the deposition chamber, each cycle depositing a very thin metal-containing layer (usually less than one monolayer such that the growth rate on average is from about 0.2 to about 3.0 Angstroms per cycle), until a layer of the desired thickness is built up on the substrate of interest. The layer deposition is accomplished by alternately introducing (i.e., by pulsing) tantalum precursor compound(s) and reaction gases into the deposition chamber containing a semiconductor substrate, chemisorbing the precursor compound(s) as a monolayer onto the substrate surfaces, and then reacting the chemisorbed precursor compound(s) with the other co-reactive reaction gas(es). The pulse duration of precursor compound(s) and optional inert carrier gas(es) is sufficient to saturate the substrate surface. Typically, the pulse duration is from about 0.1 to about 5 seconds, preferably from about 0.2 to about 1 second.

In comparison to the predominantly thermally driven CVD, ALD is predominantly chemically driven. Accordingly, ALD is often conducted at lower temperatures than CVD. During the ALD process, the substrate temperature is maintained at a temperature sufficiently low to maintain intact bonds between the chemisorbed precursor compound(s) and the underlying substrate surface and to prevent decomposition of the precursor compound(s). The temperature is also sufficiently high to avoid condensation of the precursor compounds(s). Typically the substrate temperature is kept within the range of about 25° C. to about 400° C. (preferably about 150° C. to about 300° C.), which is generally lower than presently used in CVD processes. Thus, the first species or precursor compound is chemisorbed at this temperature. Surface reaction of the second species or reaction gas can occur at substantially the same temperature as chemisorption of the first precursor or, less preferably, at a substantially different temperature. Clearly, some small variation in temperature, as judged by those of ordinary skill, can occur but still be a substantially same temperature by providing a reaction rate statistically the same as would occur at the temperature of the first precursor chemisorption. Chemisorption and subsequent reactions could instead occur at exactly the same temperature.

For a typical ALD process, the pressure inside the deposition chamber is kept at about $10^{-4}$ torr to about 1 torr, preferably about $10^{-4}$ torr to about 0.1 torr. Typically, the deposition chamber is purged with an inert carrier gas after the vaporized precursor compound(s) have been introduced into the chamber and/or reacted for each cycle. The inert carrier gas(es) can also be introduced with the vaporized precursor compound(s) during each cycle.

The reactivity of a precursor compound can significantly influence the process parameters in ALD. Under typical CVD process conditions, a highly reactive compound may react in the gas phase generating particulates, depositing prematurely on undesired surfaces, producing poor films, and/or yielding poor step coverage or otherwise yielding non-uniform deposition. For at least such reason, a highly reactive compound might be considered not suitable for CVD. However, some compounds not suitable for CVD are superior ALD precursors. For example, if the first precursor is gas phase reactive with the second precursor, such a combination of compounds might not be suitable for CVD, although they could be used in ALD. In the CVD context, concern might also exist regarding sticking coefficients and surface mobility, as known to those skilled in the art, when using highly gas-phase reactive precursors, however, little or no such concern would exist in the ALD context.

As stated above, the use of the complexes and methods of forming films of the present invention are beneficial for a wide variety of thin film applications in semiconductor structures, particularly those using high dielectric materials or ferroelectric materials. For example, such applications include capacitors such as planar cells, trench cells (e.g., double sidewall trench capacitors), stacked cells (e.g., crown, V-cell, delta cell, multi-fingered, or cylindrical container stacked capacitors), as well as field effect transistor devices.

A specific example of where a dielectric layer is formed according to the present invention is a capacitor construction. Exemplary capacitor constructions are described with reference to FIGS. 1-3. Referring to FIG. 1, a semiconductor wafer fragment 10 includes a capacitor construction 25 formed by a method of the present invention. Wafer fragment 10 includes a substrate 12 having a conductive diffusion area 14 formed therein. Substrate 12 can include, for example, monocrystalline silicon. An insulating layer 16, typically borophosphosilicate glass (BPSG), is provided over substrate 12, with a contact opening 18 provided therein to diffusion area 14. A conductive material 20 fills contact opening 18, with material 20 and oxide layer 18 having been planarized as shown. Material 20 might be any suitable conductive material, such as, for example, tungsten or conductively doped polysilicon. Capacitor construction 25 is provided atop layer 16 and plug 20, and electrically connected to node 14 through plug 20.

Capacitor construction 25 includes a first capacitor electrode 26, which has been provided and patterned over node 20. Exemplary materials include conductively doped polysilicon, Pt, Ir, Rh, Ru, $RuO_2$, $IrO_2$, $RhO_2$. A capacitor dielectric layer 28 is provided over first capacitor electrode 26. The materials of the present invention can be used to form the capacitor dielectric layer 28. Preferably, if first capacitor electrode 26 includes polysilicon, a surface of the polysilicon is cleaned by an in situ HF dip prior to deposition of the dielectric material. An exemplary thickness for layer 28 in accordance with 256 Mb integration is 100 Angstroms.

A diffusion barrier layer 30 is provided over dielectric layer 28. Diffusion barrier layer 30 includes conductive materials such as TiN, TaN, metal silicide, or metal silicide-nitride, and can be provided by CVD, for example, using conditions well known to those of skill in the art. After formation of barrier layer 30, a second capacitor electrode 32 is formed over barrier layer 30 to complete construction of capacitor 25. Second capacitor electrode 32 can include constructions similar to those discussed above regarding the first capacitor electrode 26, and can accordingly include, for example, conductively doped polysilicon. Diffusion barrier layer 30 preferably prevents components (e.g., oxygen) from diffusing from dielectric material 28 into electrode 32. If, for example, oxygen diffuses into a silicon-containing electrode 32, it can undesirably form $SiO_2$, which will significantly reduce the capacitance of capacitor 25. Diffusion barrier layer 30 can also prevent diffusion of silicon from metal electrode 32 to dielectric layer 28.

Figure 2:
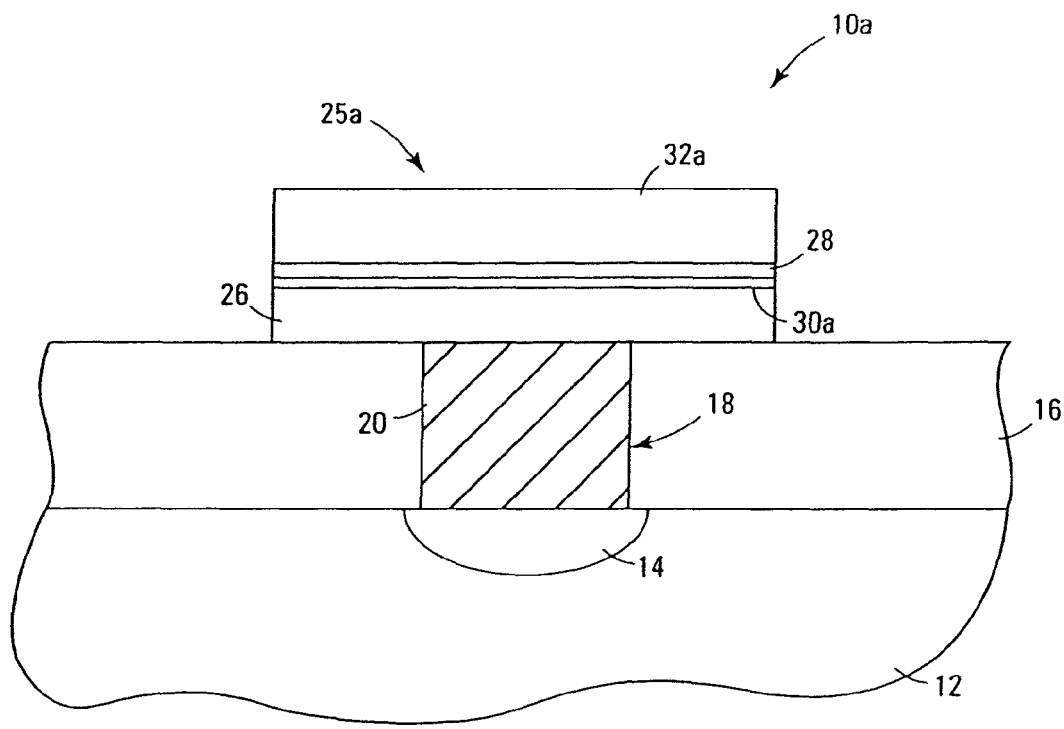

FIG. 2 illustrates an alternative embodiment of a capacitor construction. Like numerals from FIG. 1 have been utilized where appropriate, with differences indicated by the suffix "a". Wafer fragment 10a includes a capacitor construction 25a differing from the construction 25 of FIG. 2 in provision of a barrier layer 30a between first electrode 26 and dielectric layer 28, rather than between dielectric layer 28 and second capacitor electrode 32. Barrier layer 30a can include constructions identical to those discussed above with reference to FIG. 1.

Figure 3:
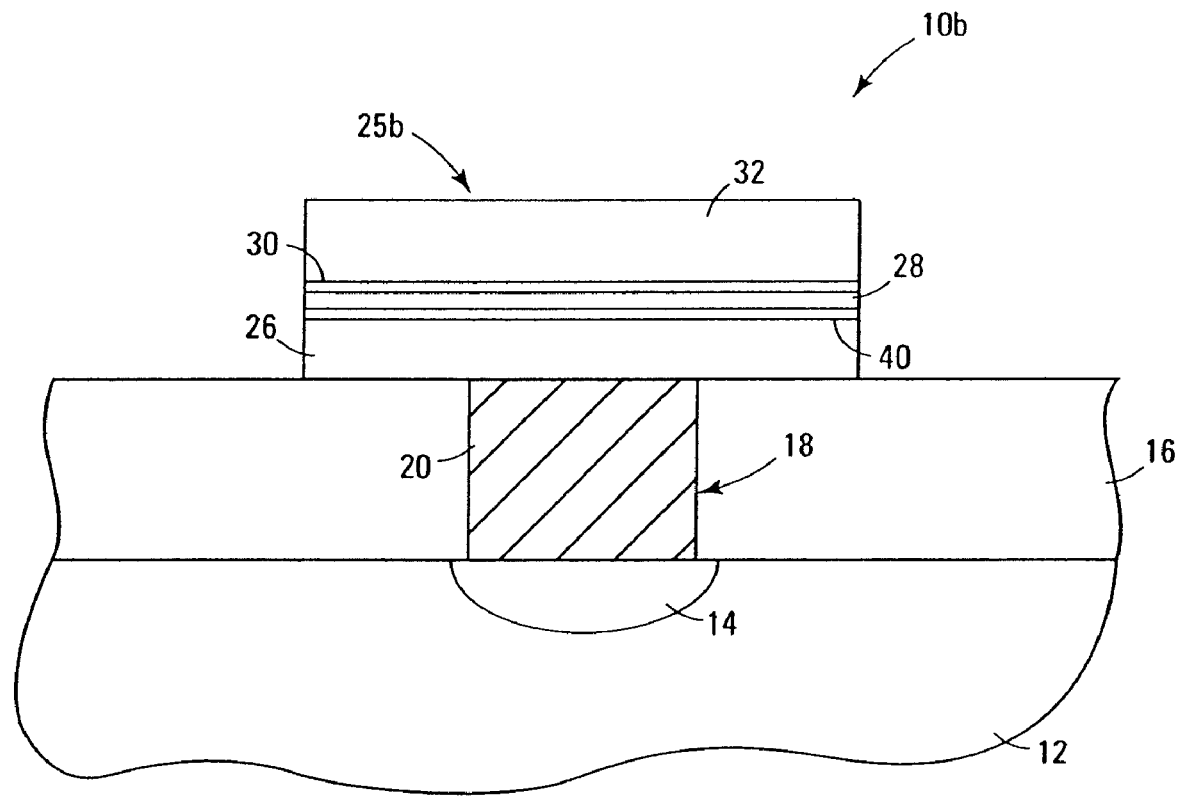

FIG. 3 illustrates yet another alternative embodiment of a capacitor construction. Like numerals from FIG. 1 are utilized where appropriate, with differences being indicated by the suffix "b" or by different numerals. Wafer fragment 10b includes a capacitor construction 25b having the first and second capacitor plate 26 and 32, respectively, of the first described embodiment. However, wafer fragment 10b differs from wafer fragment 10 of FIG. 2 in that wafer fragment 10b includes a second barrier layer 40 in addition to the barrier layer 30. Barrier layer 40 is provided between first capacitor electrode 26 and dielectric layer 28, whereas barrier layer 30 is between second capacitor electrode 32 and dielectric layer 28. Barrier layer 40 can be formed by methods identical to those discussed above with reference to FIG. 1 for formation of the barrier layer 30.

In the embodiments of FIGS. 1-3, the barrier layers are shown and described as being distinct layers separate from the capacitor electrodes. It is to be understood, however, that the barrier layers can include conductive materials and can accordingly, in such embodiments, be understood to include at least a portion of the capacitor electrodes. In particular embodiments an entirety of a capacitor electrode can include conductive barrier layer materials.

Figure 4:
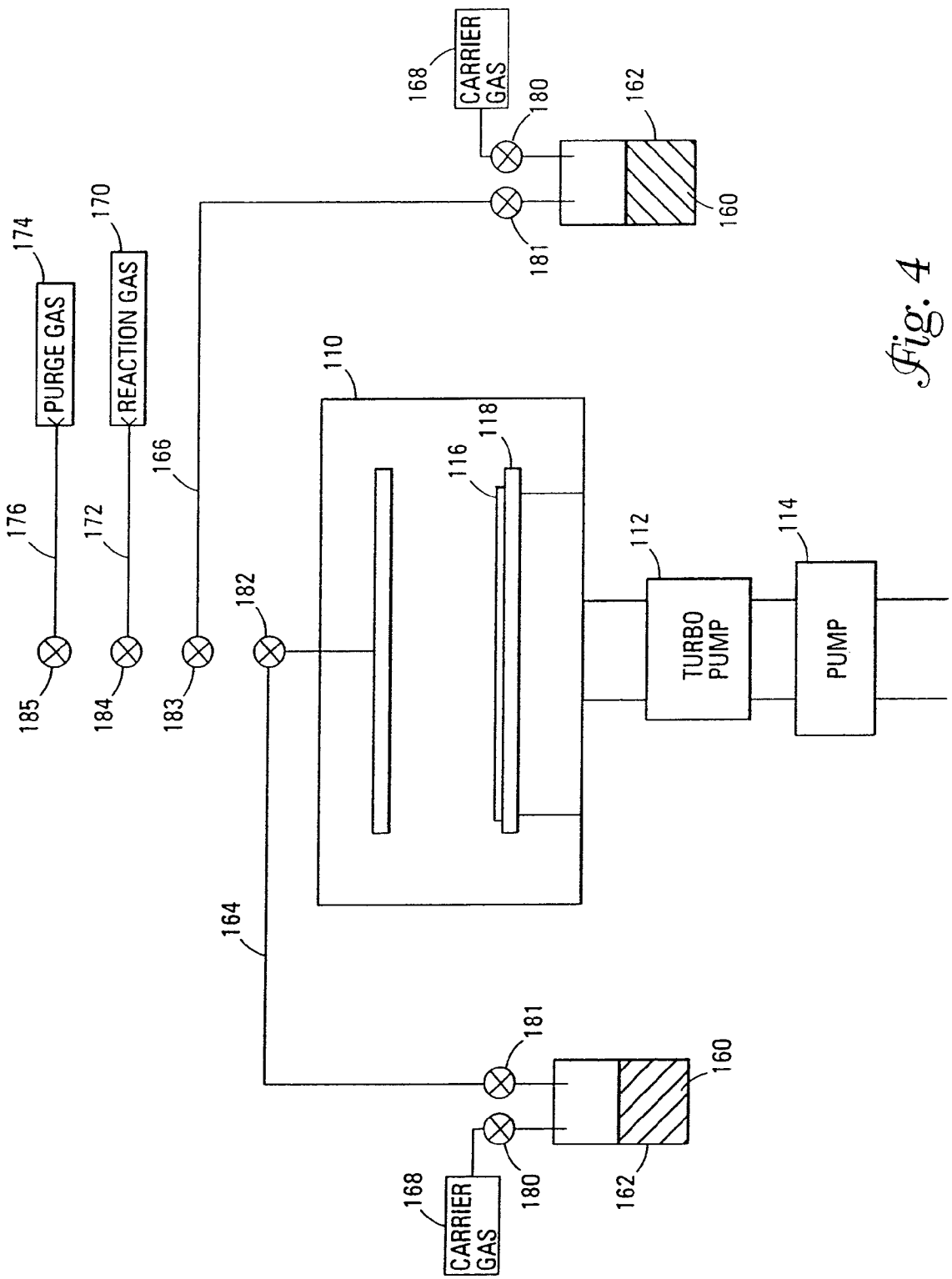
FIG. 4 is a perspective view of a vapor deposition coating system suitable for use in the method of the present invention.

A system that can be used to perform vapor deposition processes (chemical vapor deposition or atomic layer deposition) of the present invention is shown in FIG. 4. The system includes an enclosed vapor deposition chamber 110, in which a vacuum may be created using turbo pump 112 and backing pump 114. One or more substrates 116 (e.g., semiconductor substrates or substrate assemblies) are positioned in chamber 110. A constant nominal temperature is established for substrate 116, which can vary depending on the process used. Substrate 116 may be heated, for example, by an electrical resistance heater 118 on which substrate 116 is mounted. Other known methods of heating the substrate may also be utilized.

In this process, precursor compounds 160 (e.g., a tantalum precursor compound) are stored in vessels 162. The precursor compounds are vaporized and separately fed along lines 164 and 166 to the deposition chamber 110 using, for example, an inert carrier gas 168. A reaction gas 170 may be supplied along line 172 as needed. Also, a purge gas 174, which is often the same as the inert carrier gas 168, may be supplied along line 176 as needed. As shown, a series of valves 180-185 are opened and closed as required.

The following examples are offered to further illustrate the various specific and preferred embodiments and techniques. It should be understood, however, that many variations and modifications may be made while remaining within the scope of the present invention, so the scope of the invention is not intended to be limited by the examples. Unless specified otherwise, all percentages shown in the examples are percentages by weight.

EXAMPLES

Example 1

Synthesis of $Ta(OEt)_4(OCH_2CH_2O^iPr)$

Tantalum(V) ethoxide (10 mL, 15.66 g, 38.55 mmol, purchased from Schumacher Carlsbad, Calif.) and 2-isopropoxyethanol (4.5 mL, 4.06 g, 38.55 mmol, purchased from Aldrich Chemical Co, Milwaukee, Wis.) were stirred neat under reflux for approximately two hours and then allowed to reach room temperature. The reaction mixture was then stirred neat for an additional 24 hours. Using a fractional distillation column, the product was collected ($T_{bp}$=135° C., $P_{manifold}$=138 mm torr). Characterization was done by GCMS, which indicated a single product with characteristic mass peaks for the product.

Example 2

Atomic Layer Deposition of $Ta_2O_5$

The deposition of $Ta_2O_5$ was carried out using alternating pulses of $Ta(OEt)_4(OCH_2CH_2O'Pr)$ and water vapor in an ALD process. The tantalum precursor was held at 90° C. and delivered using 5 sccm helium carrier gas. The substrate was a PVD-deposited platinum bottom electrode of 100 nm thick and was held at 240° C. during 600 cycles. The film formed was approximately 320 Angstroms thick. The dielectric constant was measured using a flat capacitor test structure of sputtered platinum top electrode on top of the $Ta_2O_5$. The dielectric constant was near 40 at 0.1-100 kHz and leakage between $10^{-6}$ and $\times 10^{-8}$ $A/cm^2$ at 1 V.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A compound of the formula $Ta(OR^1)_x(O-R^2-OR^3)_y$, wherein $R^3$ is isopropyl, $R^1$ and $R^2$ are each independently a (C1-C10) organic group, x=3-4, and y=1-2.

2. The compound of claim 1 wherein $R^1$ and $R^2$ are each independently a (C1-C5) organic group.

3. The compound of claim 2 wherein $R^1$ and $R^2$ are each independently a (C1-C3) organic group.

4. The compound of claim 3 wherein $R^1$ and $R^2$ are each independently a (C1-C2) organic moiety.

5. The compound of claim 4 which is $Ta(OEt)_4(OCH_2CH_2O^iPr)$ or $Ta(OMe)_4(OCH_2CH_2O^iPr)$ wherein Me=methyl, Et=ethyl, and $^iPr$=isopropyl.

6. The compound of claim 1 wherein x=4 and y=1.

7. The compound of claim 1 wherein the compound is in the form of a neat liquid.

8. The compound of claim 5 which is $Ta(OEt)_4(OCH_2CH_2O^iPr)$.

9. The compound of claim 8 wherein the $Ta(OEt)_4(OCH_2CH_2O^iPr)$ is in the vapor phase.

10. The compound of claim 9 in combination with an inert carrier gas.

11. The compound of claim 8 in combination with one or more compounds different than $Ta(OEt)_4(OCH_2CH_2O^iPr)$.

12. The compound of claim 5 which is $Ta(OMe)_4(OCH_2CH_2O^iPr)$.

13. The compound of claim 12 wherein the $Ta(OMe)_4(OCH_2CH_2O^iPr)$ is in the vapor phase.

14. The compound of claim 13 in combination with an inert carrier gas.

15. The compound of claim 12 in combination with one or more compounds different than $Ta(OMe)_4(OCH_2CH_2O^iPr)$.

16. The compound of the claim 1 wherein at least one of $R^1$ and $R^2$ comprises at least one of a fluorine atom or a silicon atom.

17. The compound of claim 16 wherein the at least one of a fluorine atom or a silicon atom comprises a fluorine atom.

18. The compound of claim 17 wherein the fluorine atom is bonded to a carbon atom.

19. The compound of claim 17 wherein the compound is in the form of a neat liquid.

20. The compound of claim 16 wherein the at least one of a fluorine atom or a silicon atom comprises a silicon atom.

21. The compound of claim 20 wherein at least one of $R^1$, $R^2$, and $R^3$ comprises at least one fluorine atom.

22. The compound of claim 20 wherein $R^1$ and $R^2$ are each independently a (C1-C5) organic group.

23. The compound of claim 22 wherein $R^1$ and $R^2$ are each independently a (C1-C3) organic group.

24. The compound of claim 20 wherein the compound is in the form of a neat liquid.

* * * * *

UNITED STATES PATENT AND TRADEMARK OFFICE
CERTIFICATE OF CORRECTION

| | |
|---|---|
| PATENT NO. | : 7,858,815 B2 |
| APPLICATION NO. | : 12/106510 |
| DATED | : December 28, 2010 |
| INVENTOR(S) | : Brian A. Vaartstra et al. |

It is certified that error appears in the above-identified patent and that said Letters Patent is hereby corrected as shown below:

In column 1, line 6, delete "(pending)," and insert -- issued as U.S. Pat. No. 7,368,402, --, therefor.

Signed and Sealed this
Eighth Day of March, 2011

David J. Kappos
*Director of the United States Patent and Trademark Office*